(12) United States Patent
Guenin et al.

(10) Patent No.: US 6,180,121 B1
(45) Date of Patent: Jan. 30, 2001

(54) FRAGRANCE ENHANCING COMPOSITIONS FOR COSMETIC PRODUCTS

(75) Inventors: Eric P. Guenin, Hopewell Township, NJ (US); Pierre Gabriel Boudot; Pascal Michel Pierre Sillon, both of Nanterre (FR); Paul Joseph Vincenti, Jefferson; Cuthbert Donald Taylor, Kendall Park, both of NJ (US); Philippe Michel Durand, Hythe (GB)

(73) Assignee: Colgate-Palmolive Company, New York, NY (US)

( * ) Notice: Under 35 U.S.C. 154(b), the term of this patent shall be extended for 0 days.

(21) Appl. No.: 09/213,625

(22) Filed: Dec. 18, 1998

Related U.S. Application Data

(60) Provisional application No. 60/076,861, filed on Mar. 5, 1998.

(51) Int. Cl.[7] .............. A61K 7/00; A61K 7/32; A61K 7/34; A61K 7/38; A61K 7/46
(52) U.S. Cl. .............. 424/401; 424/65; 424/66; 424/68; 512/1; 512/5; 512/8; 512/25
(58) Field of Search .............. 424/401, 65, 66, 424/68; 512/1, 5, 8, 25

(56) References Cited

U.S. PATENT DOCUMENTS

| | | |
|---|---|---|
| 2,617,754 | 11/1952 | Neely . |
| 2,627,938 | 2/1953 | Frohmader et al. . |
| 2,628,187 | 2/1953 | Frohmader et al. . |
| 3,957,969 | 5/1976 | Fujiyama et al. . |
| 4,032,588 | 6/1977 | Tomita et al. . |
| 4,164,564 | 8/1979 | Chen . |
| 4,906,454 * | 3/1990 | Melanson, Jr. et al. .............. 424/47 |
| 5,063,044 | 11/1991 | Kohl et al. . |
| 5,100,655 | 3/1992 | Takano et al. . |
| 5,114,717 | 5/1992 | Kuznitz et al. . |
| 5,135,747 * | 8/1992 | Faryniarz et al. .............. 424/401 |
| 5,198,210 | 3/1993 | Critchley et al. . |
| 5,198,218 * | 3/1993 | Kuznitz et al. .............. 424/401 |
| 5,206,020 | 4/1993 | Critchley et al. . |
| 5,346,885 * | 9/1994 | Mimoun et al. .............. 512/15 |
| 5,462,691 | 10/1995 | Shimada et al. . |
| 5,525,589 * | 6/1996 | Etzweiler et al. .............. 512/23 |
| 5,540,853 * | 7/1996 | Trinh et al. .............. 510/101 |
| 5,585,092 * | 12/1996 | Trandai et al. .............. 424/65 |
| 5,585,093 * | 12/1996 | Murphy .............. 424/65 |
| 5,601,809 | 2/1997 | Davis . |
| 5,711,941 * | 1/1998 | Behan et al. .............. 424/65 |
| 5,723,420 * | 3/1998 | Wei et al. .............. 510/101 |
| 5,861,143 * | 1/1999 | Peterson et al. .............. 424/65 |

FOREIGN PATENT DOCUMENTS

| | | |
|---|---|---|
| 0463496 | 1/1992 | (EP) . |
| 0545556 | 6/1993 | (EP) . |
| 0760243 | 8/1995 | (EP) . |
| 9730689 | 2/1996 | (EP) . |
| 884688 | 12/1961 | (GB) . |
| 6126917 | 5/1988 | (JP) . |
| WO 98/35650 | 8/1998 | (WO) . |

OTHER PUBLICATIONS

*International Journal of Cosmetic Science*, vol. 5, 1983, pp. 85–95.
*Chemical Senses*, vol. 13, No. 3, pp. 463–471.
*Chemical Senses*, vol. 18, No. 3, pp. 245–256.
*Journal Society of Cosmetic Chemists*, vol. 3, 1951, pp. 30–76.
*Journal Society of Cosmetic Chemists*, vol. 1, 1947, pp. 304–310.

* cited by examiner

*Primary Examiner*—Shelley A. Dodson
*Assistant Examiner*—Marina Lamm
(74) *Attorney, Agent, or Firm*—Rosemary M. Miano

(57) ABSTRACT

This invention relates to fragrance enhancing compositions which are capable of controlling malodor from a human body to a significant extent thereby reducing the overall amount of fragrance required to achieve a satisfactory cosmetic product, especially an underarm product. The fragrance enhancing compositions of this invention are made by combining at least three components from a selected group of non-nitromusk materials.

6 Claims, No Drawings

FRAGRANCE ENHANCING COMPOSITIONS FOR COSMETIC PRODUCTS

This application claims the benefit of U.S. Provisional Application Ser. No. 60/076,861, filed Mar. 5, 1998.

FIELD OF THE INVENTION

This invention relates to fragrance enhancing compositions which may be used in a variety of products, especially in underarm products such as deodorants and antiperspirants, to give a deodorant effect against malodor from underarm perspiration and enhance the performance of the fragrance components of such products.

BACKGROUND OF THE INVENTION

A variety of approaches have been and continue to be taken for reducing and or eliminating human body malodor, especially from underarm perspiration. These approaches include reducing/eliminating perspiration itself, reducing/eliminating odor at the root cause (for example, interfering with the degradation of perspiration on skin caused by the action of bacteria) as well as masking the odors themselves.

U.S. Pat. No. 5,540,853 to Trinh et al describes personal treatment compositions and cosmetic compositions containing enduring perfume wherein the enduring perfume is evaluated by a "calculated log P" parameter. PCT application WO 97/30689 to Trinh et al describes personal treatment compositions which can be used as leave-on products which are evaluated by the same criteria.

EP patent application 0 760 243 A1 to Groverman et al describes the use of allylic perfumes as a malodor reduction agent.

EP patent application 0 545 556 A2 to Behan et al teaches a perfume composition containing at least 50% by weight of specific components (in minimum percentages of each component) selected from the group consisting of ethers, salicylates, alcohols, acetate/propionate esters and methyl ethyl ketones where members of at least 4 of the groups must be included.

U.S. Pat. No. 5,601,809 teaches the neutralization of axillary malodor.

Various references which describe evaluation of underarm deodorants or methods of evaluating products used as deodorants include P. M. Baxter et al, *International Journal of Cosmetic Science*, Volume 5, 85–95 (1983); *Chemical Senses*, Volume 13, No. 3, 463–471 (1988); J. A. Killian, *J. Soc. Cosmetic Chemists*, Volume 3, 30–76 (1952), incorporated by reference in their entirety herein.

Specific studies of selected fragrance agents include A. Baydar et al, *Chemical Senses*, Volume 18, No. 6, 661–668 (1993) (olfactory threshold for androstenone and galaxolide); *Chemical Senses*, Volume 18, No. 3 245–256 (1993) (mutual cross adaptation of the volatile steroid androstenone and a non-steroid perceptual analog); L. J. Flett, *J. Soc. Cosmetic Chemists*, Volume 1, 304–310 (1949) deodorant properties of nacconol).

U.S. Pat. No. 5,354,737 to Barr et al describes selected fragrancing compositions such as Tonalid in deodorant products.

There is still a need, however, for improving the way that cosmetic compositions are fragranced. Thus it is an object of the invention to provide fragrancing compositions which are useful in controlling malodor, especially underarm malodor. It is another object of this invention to provide fragrance enhancing components of a fragrance system for cosmetic products so that the amount of the overall fragrance components can be reduced. It is a further object of the invention to provide fragrance enhancing components that improves the performance of conventional fragrancing products. It is still another object of the invention to reduce the overall irritation potential of cosmetic products by reducing the amount of fragrance needed to provide a satisfactory product. It is also an object of the invention to provide fragrancing compositions which exhibit improved ability to mask underarm odor. It is yet another object of the present invention to provide improved underarm products such as deodorants and antiperspirants containing such fragrancing compositions. These and other objects of the invention will become apparent from the following description of the invention.

SUMMARY OF THE INVENTION

This invention relates to fragrance enhancing compositions which are capable of controlling malodor from a human body to a significant extent thereby reducing the overall amount of fragrance required to achieve a satisfactory cosmetic product, especially an underarm product. The fragrance enhancing compositions of the invention are formulated with selected components with high olfactory impact properties and good substantivity (for example, 24 hour endurance) which are combined for controlling human malodor, especially underarm sweat malodor. The fragrances made with the fragrance enhancing compositions of this invention are long lasting (enduring) as evaluated by accepted panel evaluations. By using the compositions of this invention it may also be possible to lower the amount of fragrance normally used in such cosmetic products (usually in the range of 0.1–10% by weight based on the total weight of the cosmetic composition) to some lesser amount.

The fragrance enhancing compositions of this invention are made by combining at least three components from the group consisting of the following non-nitromusk materials:

(1) Cinnamon Leaf Oil Ceylan {a Natural Essential Oil—predominantly 2-methoxy 4 allyl phenol};
(2) Vetiver Oil Java {a Natural Essential Oil—predominantly Vetiverol alcohol};
(3) Orange Oil Morocco {a Natural Essential Oil—predominantly d-Limonene};
(4) Patchouli Oil {a Natural Essential Oil—predominantly Patchouli Alcohol and Patchoulene};
(5) Iso Methyl Cedryl Ketone A {a multi-component proprietary formulation available from Fragrance Resources, Keyport, N.J.; {this material is predominantly comprised of esters with additional minor amounts of alcohols, essential oils, terpenes and others};
(6) Pelargonyl {a multi-component proprietary formulation available from Synarome, Bois Colombes, France; this material is comprised of mostly ethers with some portions of esters, alcohols and terpenes};
(7) Cassis 345 B {a multi-component proprietary formulation available from Firmenich SA, Geneva, Switzerland; this material is primarily composed of alcohols and esters with minor amounts of natural extracts from essential oils};
(8) nonyl aldehyde;
(9) decyl aldehyde;
(10) Ambroxan® {8-alpha, 12-oxido-13,14,15,16-tetranorlabdane or 3aR-(3a,alpha,5a,alpha,9a,beta,9b,beta))-dodecahydro-3a,6,6,9a-tetramethylnaphthto(2,1-b)furan};
(11) Alpha-Iso-Amyl-Cinnamic {amyl cinnamic aldehyde};
(12) benzyl propionate;

(13) Carvone Laevo {L-1-methyl-4-isopropenyl-6-cyclohexene-2-one };
(14) Beta-Gamma Hexenyl Salicylate {cis-3-hexenyl salicylate};
(15) Citral {3,7-dimethyl-2,6-octadienal};
(16) Citronellol Dextro {3-7-dimethyl-6-octen-1-ol};
(17) Cyclamen Aldehyde {2-methyl-3-(para-isopropylphenyl)propionaldehyde};
(18) Damascone Alpha {2-buten-1-one, 1-(2,6,6-trimethyl-2-cyclohexen-1-yl)};
(19) Decyl Aldehyde Natural { Decanal Natural};
(20) Ethyl Vanillin {3-ethoxy-4-hydrobenzaldehyde};
(21) Eugenol {2-methoxy-4-allyl phenol};
(22) Florazon {4-ethyl-alpha, alpha-dimethyl-benzenepropanal};
(23) Geraniol {2-trans-3,7-dimethyl-2,6-octadien-8-ol};
(24) Herbanate {3-(1-methyl-ethyl) bicyclo (2,2,1) hept-5-ene-2-carboxylic acid ethyl ester};
(25) Iso Butyl Quinoleine {6-secondary butyl quinoline};
(26) Menthol Laevo {5-methyl-2-isopropyl cyclohexanol};
(27) Menthone Laevo { 4-isopropyl-l-methyl cyclohexan-3-one};
(28) Iralia Total® {Methyl Ionone (mixture of isomers)};
(29) Methyl Ionone Gamma Coeur {3-buten-2-one, 3 methyl-4-(2,6,6-trimethyl-2-cyclohex-1-yl};
(30) para-hydroxy phenyl butanone crystals {4-(4-hydroxyphenyl)-2-butanone};
(31) 4-methyl-2-phenyl-3,6-dihydropyrane;
(32) Rootanol 100® {2-(1,1-dimethylethyl)-4-methyl-cyclohexanol};
(33) Terpineol Alpha {1-methyl-4-isopropyl-1-cyclohexen-8-ol};
(34) Vanillin {4-hydroxy-3-methoxy benzaldehyde}; and
(35) 2,4-diethoxy-5-methyl-pyrimidine}.

DETAILED DESCRIPTION OF THE INVENTION

The term "Deo-Key™" is applied here to fragrance enhancing compositions which provide an improved way to control malodor, especially underarm malodor either alone or in combination with other fragrances of the type conventionally used in cosmetic compositions, especially those used in underarm products. The fragrance enhancing compositions (also called fragrance enhancing components herein) are made by combining at least three (and more particularly five) members of the group consisting of the thirty-five ingredients listed above in proportions as follows wherein the amounts are based on the total amount of the fragrance component in the cosmetic product:
(a) 0.5-1.0% Cinnamon Leaf Oil Ceylan;
(b) 0.01–0.3% Vetiver Oil Java;
(c) 0.5–6.0% Orange Oil Morocco;
(d) 0.05–6.0% Patchouli Oil;
(e) 0.05–4.0% Iso Methyl Cedryl Ketone A;
(f) 0.05–6.0% Pelargonyl;
(g) 0.05–0.9% Cassis 345 B;
(h) 0.005–0.05% nonyl Aldehyde;
(i) 0.005–0.05% decyl Aldehyde;
(j) 0.05–0.30% 3aR-(3a,alpha,5a,alpha,9a,beta,9b,beta))-dodecahydro-3a,6,6,9a-tetramethyl-naphthto(2,1-b)furan;
(k) 0.05–10.0% amyl cinnamic aldehyde;
(l) 0.05–0.9% benzyl propionate;
(m) 0.05–0.30% L-1-methyl-4-isopropenyl-6-cyclohexene-2-one;
(n) 0.05–0.30% cis-3-hexenyl salicylate;
(o) 0.05–0.70% 3,7-dimethyl-2,6-octadienal;
(p) 0.05–2.00% 3-7-dimethyl-6-octen-1-ol;
(q) 0.05–0.9% 2-methyl-3-(para-isopropylphenyl) propionaldehyde;
(r) 0.05–0.9% 2-buten-1-one, 1-(2,6,6-trimethyl-2-cyclohexen-1-yl);
(s) 0.005–0.05% decyl aldehyde Natural;
(t) 0.05–0.3% 3-ethoxy-4-hydrobenzaldehyde;
(u) 0.05–1.00% 2-methoxy-4-allyl phenol;
(v) 0.05–0.30% 4-ethyl-alpha, alpha-dimethyl-benzenepropanal;
(w) 0.05–6.0% 2-trans-3,7-dimethyl-2,6-octadien-8-ol;
(x) 0.05–4.0% 3-(1-methyl-ethyl) bicyclo (2,2,1) hept-5-ene-2-carboxylic acid ethyl ester;
(y) 0.05–0.30% isobutyl quinoleine;
(z) 0.05–2.0% 5-methyl-2-isopropyl cyclohexanol;
(aa) 0.05–0.3% 4-isopropyl-1-methyl cyclohexan-3-one;
(bb) 0.05–2.0% methyl ionone (mixture of isomers);
(cc) 0.05–2.0% 3-buten-2-one, 3 methyl-4-(2,6,6-trimethyl-2-cyclohex-1-yl;
(dd) 0.05–0.90% para-hydroxy phenyl butanone crystals;
(ee) 0.05–4.0% 4-methyl-2-phenyl-3,6-dihydropyrane;
(ff) 0.05–0.30% 2-(1,1-dimethylethyl)-4-methyl-cyclohexanol;
(gg) 0.05–6.0% 1-methyl-4-isopropyl-1-cyclohexen-8-ol;
(hh) 0.05–0.3% 4-hydroxy-3-methoxy benzaldehyde; and
(ii) 0.05–0.3% 2,4-diethoxy-5-methyl-pyrimidine.

For cosmetic compositions an amount of 1.8–100%, particularly 1.8–60%, more particularly 1.8–35%, with a specific range being 1.8–32.5%, and more specific ranges being 2.5–30%, 25–27%, and 20% by weight based on the total amount of fragrance component added to make the cosmetic composition can be used to achieve the desired effect. It is also possible that a major portion of the fragrance portion such as 60–90% of the fragrance portion and even 100% of the fragrance portion is made of the fragrance enhancing compositions described for this invention.

The use of the fragrance enhancing compositions make the use of conventional fragrances more effective in controlling underarm malodor and may also result in the ability to use lower amounts of fragrances to achieve performance equivalent to compositions not containing such fragrance enhancing compositions. Although it is possible to use the fragrance enhancing compositions of this invention as the sole fragrance in cosmetic products such as deodorants and/or antiperspirants, it has been found preferable (for aesthetic reasons to give a more rounded fragrance) to use at least a portion of conventional fragrances in the cosmetic compositions.

The conventional fragrances that can be combined with the fragrance enhancing compositions of the invention include those described in PCT application WO 97/30689 and incorporated by reference in its entirety herein. Specific non-limiting examples of suitable fragrances include those selected from the group consisting of those described therein. Specific groups include:
(a) esters of salicylic acid such as hexyl salicylate, hexenyl salicylate, isoamyl salicylate, benzyl salicylate and cyclohexyl salicylate;
(b) esters of cinnamic acid such as amyl cinnamate, cinnamyl cinnamate and methyl cinnamate;
(c) miscellaneous esters such as allyl cyclohexane propionate, amyl benzoate, para-tertiarybutylcyclohexyl acetate, cedryl acetate, cedryl formate, dihydro-isojasmonate, ethylene brassylate, ethyl undecylenate, geranyl anthranilate, geranyl phenyl acetate, linalyl benzoate, benzyl acetate, linalyl acetate, vetiveryl acetate;
(d) aldehydes such as amyl cinnamic aldehyde, cyclamen aldehyde, lillial, benzaldehyde, citronnelal, hydroxy-citronellal;

(e) alcohols such as geraniol, linalool, nerol, phenyl ethyl alcohol, alpha terpineol, eugenol, isoeugenol, alpha-citronellol, dihydromyrcenol, aurantiol, cedrol, phenyl heptanol, phenol hexanol, alpha-santalol, undecavertol (4-methyl-3-decen-5-ol), benzyl alcohol;

(f) ketones such as benzophenone, dodecalactone, gamma-n-methyl ionone, delta-undecalactone, gamma-undecalactone, laevo-carvone, beta-methylnaphthyl ketone;

(g) nitromusk such as musk ketone, musk tibetine, musk indanone.

The individual components listed above used to form the fragrance enhancing compositions of this invention are commercially available and may be obtained from suppliers of fragrances and specialty chemicals who are known to those skilled in the art.

The ability of the fragrance enhancing components of the invention to improve the performance of conventional fragrances may in some cases be due to synergy between the various components of the overall fragrance component (the total of all fragrance ingredients used in a cosmetic product).

Each of the thirty-five components listed above have a sensory sniff rating as evaluated by panel tests. Such tests are described in the art and are well accepted as being appropriate ways of evaluating overall fragrance impact and effect. An example of one such test is described in International Journal of Cosmetic Science, Volume 5, pages 85–95 (1983). In such tests numerical rating scales are used to establish the relative performance of each fragrance. One such scale is, for example 0–5 (0 means a high performance, 5 a poor performance). On such a scale the individual compositions listed above as the group from which the fragrance enhancing compositions would be made would each have a rating between 0–2. Such fragrance raw materials improve deodorancy and longevity of cosmetic products (for example, deodorant sticks) in conjunction with fragrance aesthetics. Since fragrances are sometimes responsible for skin irritation, it is also a benefit of the present invention that the overall amount of fragrance in a cosmetic products can be reduced by the use of the compositions of this invention.

The cosmetic compositions can include one or more active ingredients selected from, for example, a member selected from the group consisting of antiperspirant active materials, deodorant active materials, sunscreens, insect repellents, antifungal agents, antimicrobials (also called bacteriostats or antibacterials), and additional fragrances.

Where the composition contains an antiperspirant active, any of the known antiperspirant active materials can be utilized. These can be added as solutions, suspensions or directly during mixing. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Antiperspirant actives can be incorporated into compositions according to the present invention in amounts in the range of 0.1–30%, preferably 15–25%, by weight, of the total weight of the composition. The amount used will depend on the formulation of the composition. For example, at amounts in the lower end of the broader range (for example, 0.1–10%), the antiperspirant active material will not substantially reduce the flow of perspiration, but will reduce malodor, for example, by acting as an antimicrobial material.

For embodiments of the invention which contain an antiperspirant (either at a level denominated "deodorant" or at a level denominated "antiperspirant") it is preferred that a stabilizing agent also be included. Examples of suitable stabilizing agents include cosmetically acceptable alkali metal salts, bases, amines and other nitrogen containing compounds, particularly guanidine carbonate (described in U.S. Pat. No. 5,490,979 and assigned to the same owner as this application).

When a bacteriostat composition is included in the cosmetic products of this invention such known bacteriostats may include bacteriostatic quaternary ammonium compounds (such as cetyl-trimethylammonium bromide), 2-amino-2-methyl-1-propanol (AMP), cetyl pyridinium chloride, 2,4,4'-trichloro-2'-hydroxydiphenylether (Triclosan), N-(4-chlorophenyl)-N'-(3,4-dichlorophenyl) urea (Triclocarban) and various zinc salts (for example, zinc ricinoleate). The bacteriostat can, illustratively, be included in the composition in an amount of 0.01–1.0% by weight, of the total weight of the composition. Triclosan, can illustratively be included in an amount of from 0.05% to about 0.5% by weight, of the total weight of the composition.

If sunscreens are used conventional agents may be included.

The base for cosmetic compositions made with the fragrancing materials of this invention include soap based deodorants, especially those made with one or more glycols (propylene glycol, dipropylene glycol, tripropylene glycol, tetrapropylene glycol and/or other polypropylene glycols); silicone based deodorants and antiperspirants, especially those made with fatty alcohols.

Products made as cosmetic compositions may include antiperspirants and/or deodorants, deodorant soaps, body washes, creams, lotions, scented cosmetic products such as colognes and perfumes.

In one embodiment for a deodorant stick with such efficacy, fragrance raw materials should be used in an amount between 0.001% and 25.00% of the fragrance (neat composition) portion of the composition, particularly between 0.001% and 20.00%, more preferably between 0.05% and 15.00% of the fragrance, and even more preferably between 0.50% and 10.00% of the fragrance.

Deo-Key™ compositions combine fragrance raw materials such as examples described below. The examples listed below describe compositions used in a range of 1.8–32.6% based on the total fragrance component. For example 30% of a fragrance used at a 10% level would give a maximum level for the Deo-Key composition of 3.00% by weight of the overall cosmetic product. The following embodiments show how ranges of various fragrance components can be combined wherein the amounts listed are percents of the total fragrance component (unless another standard is listed such as "overall product").

| Green Deo ™ Fragrance Enhancer | Range A | Range B |
|---|---|---|
| Cassis 345 B | 0.20–1.50 | 0.40–0.90 |
| Damascone Alpha | 0.20–1.50 | 0.40–0.90 |
| Para Hydroxy Phenyl Butanone Crystals | 0.20–1.50 | 0.40–0.90 |
| Herbanate | 1.00–5.00 | 2.00–4.00 |
| Rosyrane | 1.00–5.00 | 2.00–4.00 |
| Total | 2.60–14.50 | 5.2–10.7 |

In another embodiment the Green Deo-Key fragrance can be used in an amount of from 25–27% of the total fragrance component (which is greater than the specifically described 2.60–14.50 amount), provided that the ratios of the individual ingredients are maintained in the same ranges as described for the 2.60–14.50 composition).

| Wood Deo-Key ™ Fragrance Enhancer | Range A | Range B |
|---|---|---|
| Vanillin | 0.02–0.50 | 0.05–0.30 |
| Vethymine | 0.02–0.50 | 0.05–0.30 |
| Ambroxan | 0.02–0.50 | 0.05–0.30 |
| Benzenepropanal, 4 ethyl-alpha, alpha-dimethyl {Florazon 3/034395} | 0.02–0.50 | 0.05–0.30 |
| Vetiver Oil Java | 0.02–0.50 | 0.05–0.30 |
| Iso Methyl Cedryl Ketone A | 1.00–5.00 | 2.00–4.00 |
| Terpineol Alpha | 1.00–5.00 | 2.00–4.00 |
| Patchouli Oil | 2.00–8.00 | 3.00–6.00 |
| Amyl Cinnamic Aldehyde | 4.00–12.00 | 6.00–10.00 |
| Total | 8.10–32.50 | 13.2–25.5 |

| Floral Wood Deo-Key ™ Fragrance Enhancer | Range A | Range B |
|---|---|---|
| Damascone Alpha | 0.02–0.50 | 0.05–0.30 |
| Rootanol 100 | 0.02–0.50 | 0.05–0.30 |
| Carvone Laevo | 0.02–0.50 | 0.05–0.30 |
| Benzyl Propionate | 0.20–1.20 | 0.40–0.90 |
| Cyclamen Aldehyde | 0.50–2.50 | 1.00–2.00 |
| Orange Oil Morocco | 2.00–8.00 | 3.00–6.00 |
| Citronellol Dextro | 2.00–8.00 | 3.00–6.00 |
| Pelargonyl | 2.00–8.00 | 3.00–6.00 |
| Total | 6.76–29.20 | 10.6–21.8 |

| Citrus Wood Deo-Key ™ Fragrance Enhancer | Range A | Range B |
|---|---|---|
| Nonyl Aldehyde | 0.002–0.1 | 0.005–0.05 |
| Decyl Aldehyde | 0.002–0.1 | 0.005–0.05 |
| Cis-3-Hexenyl Salicylate | 0.02–0.4 | 0.05–0.30 |
| Citral Lemarome | 0.02–0.4 | 0.05–0.30 |
| Cyclamen Aldehyde | 0.20–1.20 | 0.40–0.90 |

-continued

| Citrus Wood Deo-Key ™ Fragrance Enhancer | Range A | Range B |
|---|---|---|
| Citronellol Dextro | 0.8–2.40 | 1.00–2.00 |
| Iralia Total | 0.8–2.40 | 1.00–2.00 |
| Total | 1.84–7.00 | 2.5–5.6 |

| Amber Wood Deo-Key ™ Fragrance Enhancer | Range A | Range B |
|---|---|---|
| Isobutyl Quinoleine | 0.02–0.4 | 0.05–0.30 |
| Ambroxan | 0.02–0.4 | 0.05–0.30 |
| Cinnamon Leaf Oil Ceylan | 0.4–1.20 | 0.60–1.00 |
| Eugenol | 0.4–1.20 | 0.60–1.00 |
| Iso Methyl Cedryl Ketone A | 1.00–5.00 | 2.00–4.00 |
| Patchouli Oil | 2.00–7.00 | 3.00–6.00 |
| Total | 3.84–15.2 | 6.3–12.6 |

| Mint Deo-Key ™ Fragrance Enhancer | Range A | Range B |
|---|---|---|
| 4-isopropyl-1-methyl cyclohexan-3-one {Menthone Laevo} | 0.02–0.40 | 0.05–0.30 |
| Ethyl Vanillin | 0.02–0.40 | 0.05–0.30 |
| Decyl Aldehyde Natural {Decanal Natural 951512} | 0.1–0.5 | 0.15–0.40 |
| 5-Methyl 2-Isopropyl Cyclohexanol {Menthol Laevo} | 0.8–2.40 | 1.00–2.00 |
| Methyl Jonone Gamrna Coeur | 0.8–2.40 | 1.00–2.00 |
| Geraniol | 2.00–7.00 | 3.00–6.00 |
| Total | 3.74–13.10 | 5.3–11.0 |

It should be noted that other embodiments can contain more than the described totals for the compositions listed above, provided that the same ratios of the ingredients for each composition are maintained and a multiple of these ratios is used to give a total amount greater than the specific embodiments listed above. This is particularly described above in the case of the Green Deo-Key composition.

The cosmetic compositions in which this invention can be used can take various forms including sticks, gels, soft solids, creams, liquids (for example, roll-ons), and aerosols.

| INGREDIENT | RANGES | PREFERRED RANGES |
|---|---|---|
| SOLIDS | | |
| Solid Stick "A" | | |
| aluminum zirconium tetrachlorohydrex-gly | 15–25 | 18–22 |
| volatile silicone (for example cyclomethicone) | 30–60 | 45–55 |
| stearyl alcohol | 5–15 | 8–12 |
| talc | 5–15 | 8–12 |
| hydrogenated castor oil | 0–5 | 1–3 |
| PPG-14 butyl ether | 0–3 | 1–2 |

-continued

| INGREDIENT | RANGES | PREFERRED RANGES |
|---|---|---|
| fragrance component of which 2.5–30% is the Deo-Key ™ composition (for example 2% of the overall stick) | 0.1–10 | 1–3 |
| alantoin | 0.01–1 | 0.05–0.5 |
| glyceryl stearate | 0.01–1 | 0.05–0.5 |
| PEG 100 stearate | 0.01–1 | 0.05–0.5 |
| color (optional) | 0.001–0.1 | 0.005–0.05 |
| Solid Stick "B" (deodorant) | | |
| SD alcohol 40 | 10–80 | 40–70 |
| propylene glycol | 5–20 | 10–15 |
| sodium stearate | 2–10 | 6–8 |
| water | 0–20 | 10–15 |
| fragrance component of which 2.5–30% is the Deo-Key ™ composition | 0.1–1.0 | 1–3 |
| trisodium EDTA | 0.05–0.5 | 0.1–0.4 |
| color (optional) | 0.001–0.01 | 0.005–0.01 |
| Solid Stick C (deodorant) | | |
| Solvent (selected from a range of glycols as described for Stick "D") | 5–88 | 60–75 |
| water | 1–50 | 10–20 |
| compatible gelling agent | 1–10 | 4–8 |
| emollient | 0–5 | 1–2 |
| antibacterial agent | 0.01–2.0 | 0.05–0.5 |
| anti-irritancy agent | 0.1–10 | 1–3 |
| fragrance component of which 2.5–30% is the Deo-Key ™ composition (for example 2% of the overall stick) | 0.1–10 | 0.5–3 |
| Solid Stick D (deodorant) | | |
| glycol component (one or more of glycols such as propylene glycol, di-, tri-, tetra-, and higher propylene glycols) | 60–98 | 65–75 |
| sodium stearate | 0–10 | 6–8 |
| water | 0–40 | 10–25 |
| fragrance component of which 2.5–30% is the Deo-Key ™ composition (for example 2% of the overall stick) | 0.1–10 | 0.5–3 |

| INGREDIENT | RANGES | PREFERRED RANGES |
|---|---|---|
| GELS | | |
| Gel "A" | | |
| cyclomethicone and dimethicone copolyol | 5–30 | 8–10 |
| cyclomethicone | 60–90 | 70–80 |
| aluminum chlorohydrate | 10–25 | |
| propylene glycol | 10–20 | 12–18 |
| water | 10–30 | 15–25 |
| fragrance component of which 2.5–30% is the Deo-key ™ composition (for example 2% of the overall product) | 0.5–10 | 1–3 |
| CREAMS | | |
| Cream "A" | | |
| aluminum chlorohydrate | 10–25 | 15–22 |
| aluminum chloride | 5–15 | 6–12 |
| water | 40–70 | 50–65 |

-continued

| INGREDIENT | RANGES | PREFERRED RANGES |
|---|---|---|
| glyceryl stearate | 1–20 | 5–15 |
| PEG-40 stearate | 1–20 | 5–15 |
| cetyl palmitate or synthetic spermaceti | 1–10 | 3–7 |
| glycerin | 1–10 | 2–8 |
| dimethicone | 1–10 | 2–8 |
| isopropyl palmitate | 1–10 | 2–5 |
| petrolaturn and lanolin alcohol | 1–10 | 2–6 |
| lanolin wax | 1–10 | 2–8 |
| hydroxypropyl methylcellulose | 0.5–1.5 | 0.8–1.2 |
| fragrance component of which 2.5–30% is the Deo-Key ™ composition (for example 1% of the overall product) | 0.1–10 | 1–3 |
| titaniumdioxide | 0.1–1 | 0.2–0.8 |
| lanolin | 0.5–1 | 0.6–0.8 |
| propyl paraben | 0.05– | 0.1–0.2 |
| mineral oil | 0.5–1 | 0.6–1 |
| LIQUIDS | | |
| Roll-on "A" (antiperspirant) | | |
| aluminum chlorohydrate (for example 21%) | 10–21 | 18–22 |
| water (for example 67%) | 50–80 | 65–75 |
| PPG-11 stearyl ether (for example 7%) | 5–10 | 6–8 |
| Steareth-2 (for example 5%) | 2–10 | 4–8 |
| Steareth-20 (for example 5%) | 2–10 | 4–8 |
| fragrance component of which 2.5–30% is the Deo-Key ™ composition (for example 1% of the overall product) | 0.1–10 | 1–3 |
| Roll-on "B" (antiperspirant) | | |
| zirconium-aluminum glycine hydroxychloride complex | 10–25 (for example 20%) | 18–22 |
| water | 20–40 (for example 24.3%) | 24–30 |
| PEO-40 stearate | 5–15 (for example 10%) | 8–12 |
| glyceryl stearate | 5–15 (for example 10%) | 8–12 |
| glycerine | 5–10 (for example 6.8%) | 6–8 |
| refined paraffin | 4–10 (for example 6.2%) | 5–9 |
| isopropyl palmitate | 5–10 (for example 7.3%) | 6–9 |
| magnesium aluminum silicate | 10–20 (for example 15.2%) | 12–18 |
| fragrance component of which 2.5–30% is the Deo-Key ™ composition (for example 1.5% of the overall stick) | 0.1–10 | 1–3 |
| Roll-on "C" | | |
| aluminum chlorohydrate | 10–25 (for example 21%) | 15–22 |
| cyclomethicone | 40–80 (for example 70%) | 60–70 |
| quatemium-18 hectorite | 0–6 (for example 4%) | 3–5 |
| SD alcohol 40 (3.1% by volume) | 1–4 (for example 2%) | 2.5–3.5 |
| Steareth-20 | 0–4 (for example 2%) | 1–3 |
| fragrance component of which 2.5–30% is the Deo-Key ™ composition (for example 1% of the overall product) | 0.5–10 | 1–3 |

| INGREDIENT | RANGES | PREFERRED RANGES |
|---|---|---|
| Roll-on "D" | | |
| cyclomethicone | 10–80 | 35–55 |
| cyclomethicone and dimethicone copolyol | 5–20 | 10–15 |
| aluminum zirconium tetrachlorohydrex-gly | 10–25 | 15–22 |
| propylene glycol | 5–15 | 7–12 |
| water | 0–5 | 2–4 |
| fragrance component of which 2.5–30% is the Deo-Key ™ composition | 0.5–10 | 1–3 |

Aerosols

Aerosol "A"

An aerosol formulation made with the following amounts of ingredients based on the total weight of the composition: aluminum chlorohydrate (for example 10–22%); isobutane (for example 30–45%); cyclomethicone (for example 10–20%); isopropyl myristate (for example 2–5%); dimethicone (for example 2–4%); quaternium-18 hectorite (for example 1–2%); propylene carbonate (for example 0.5–1%); effective amount of a fragrance component of which 2.5–30% is the Deo-Key™ composition (for example 1% of the overall product).

Aerosol "B"

An aerosol formulation made with the following amounts of ingredients based on the total weight of the composition: SD alcohol 40 (for example 10–30%); isobutane (for example 10–30%); propane (for example 10–20%); propylene glycol (for example 5–20%); butane (for example 5–10%); effective amount of a fragrance component of which 2.5–30% is the Deo-Key™ composition (for example 1% of the overall product); effective amount of Triclosan.

Pump Spray "A"

A pump spray formulation made with the following amounts of ingredients based on the total weight of the composition: cyclomethicone (for example 40–60%); SD alcohol 40B (anhydrous alcohol) (for example 20–40%); PEG-3 myristyl ether (for example 2–10%); C12-15 alcohol benzoates (for example 2–10%); water (for example 2–10%); effective amount of a fragrance component of which 2.5–30% is the Deo-Key™ composition; dimethicone (for example 0.5–5%); zinc phenosulfonate (for example 0.1–1.0%).

| INGREDIENT | RANGES OF INGREDIENTS | PARTICULAR EXAMPLE |
|---|---|---|
| Pump Spray "B" - wherin amounts are based on the total weight of the composition. | | |
| cyclomethicone | 30–50% | 33% |
| mineral oil | 1–10% | 2.0% |
| phenyltrimethicone | 1–10% | 5.0% |
| cyclomethicone and dimethicone copolyol | 0.5–10% | 10% |
| polysorbate 20 | 0.5–5% | 1.0% |
| aluminum chlorohydrate | 5–25% | 10–25% |
| fragrance component of which 2.5–30% of the composition is the Deo-Key ™ composition | 0.1–10 | |

EXAMPLES

The following Examples are offered as illustrative of the invention and are not to be construed as limitations thereon.

In the Examples and elsewhere in the description of the invention, chemical symbols and terminology have their usual and customary meanings. Temperatures are in degrees C unless otherwise indicated. The amounts of the components are in weight percents based on the standard described; if no other standard is described then the total weight of the compositions is to be inferred. Various names of chemical components include those listed in the CTFA *International Cosmetic Ingredient Dictionary* (Cosmetics, Toiletry and Fragrance Association, Inc., $4^{th}$ ed. 1991). Note that the antiperspirant actives described in the examples and elsewhere are usually added in the form of a solution for example as a 50% solution. Effective amounts of fragrance component are in the range of 0.–10% by weight based on the total weight of the cosmetic composition, a portion of which is described as being the Deo-Key composition.

Example 1

General Method A

The Deo-Key fragrance enhancing compositions of this invention may be made by conventional mixing techniques known to those skilled in the art. Such techniques will take into account the solid or liquid nature of the products involved and the need to pre-dissolve or melt ingredients before they are blended. The solid ingredients should be added first and dissolved or melted until a liquid is obtained by heating in a sand bath (for example, at a temperature in the range of 40–60 degrees C). The liquid ingredients may then be added in a subsequent step and the final mixture will be completed at room temperature with stirring (for example, at 500 RPM with a stirring machine AM 3000 D from HEIDOLPH).

For example, in one method the ingredients are weighed in a beaker which has been tared (such as with a PJ3600 Delta Range balance from METTLER). The total quantity of Deo-Key material should be calculated to have a minimum quantity of individual material greater than 1 gram (minimum weighable quantity). If any error occurs it should be corrected by restarting the entire weighing process; thus, this sequential methodology of weighing in the same beaker avoids the loss of ingredients during transfer from one beaker to another.

Example 2

Test samples can be prepared by taking ten 6 cm diameter (2.5 inches) circles of Webril® pads and treating them with a selected mount of test product. The test sample is rubbed or applied on one side of the pad. Each pad is then placed in a plastic disposable Petri dish which has been labeled. Each pad is allowed to dry for 24 hours at room temperature with the lid of the Petri dish removed. After the 24 hour period, a solution of synthetic malodor material is applied to each pad in an amount of about 9× excess of the sample test product by applying it to the treated surface of the pad. The solution is added dropwise to cover the entire surface of the treated pad. The sample is allowed to dry for an additional 2 hours before placing the lids on the Petri dishes. The plates are stored at room temperature until the 48 hour odor evaluation is performed. The odor assessment is done by a number of trained personnel, using some preset numerical scale.

Example 3

Testing Method for Fragrance Effectiveness Against Malodor

The Green Deo-Key™ and Woody Deo-Key™ compositions prepared by the method described in Example 1 were tested against a traditional fragrance formulation of 2.5% made as follows. Evaluations of the effectiveness of each test sample were done by a panel using a rating system of 0–7 to evaluate the effectiveness of the sample in reducing malodor. The data shown below demonstrates that 0.4% levels of the Deo-Key™ compositions listed were as effective as traditional fragrance at a level of 2.5%. This indicates that the Deo-Key™ compositions may be used at much lower levels.

| Type and Level of Deo-Key | Score | Control |
|---|---|---|
| 0.4% green Deo-Key | 0.3 | 0.4 |
| 0.4% Woody Deo-Key | 0.6 | 0.6 |

Example 4

A comparative evaluation using a panel of five trained panelists was performed. The three samples tested were Sample A1=Commercial Product A believed to contain about 2.5% of a conventional fragrance; Sample B1=a cosmetic stick formulated with 0.4% of a Green Deo-Key composition as described above; and Sample C1=the same cosmetic stick formulation as in Sample B but without the Deo-Key composition of the invention, but with 1.1% of a conventional fragrance. The evaluation results are given as an average of the ratings by the panel for perception of malodor. The higher the number the poorer the performance of the product: Sample A1—0.45; Sample B1—0.33; Sample C1—0.58.

Example 5

The procedure of Example 4 was repeated where Sample A2=Sample A1; Sample B2-=Sample B1; and Sample C2=the same cosmetic stick formulation as in B1 except that 0.6% of the Deo-Key composition was used. The evaluation data is as follows: Sample A2—0.45; Sample B2—0.33; Sample C2—0.19.

We claim:

1. A cosmetic composition made with a fragrance enhancing composition comprising 0.40–0.90% Cassis 345 B; 0.40–0.90% 2-buten-1-one, 1-(2,6,6-trimethyl-2-cyclohexen-1-yl); 0.40–0.90% para-hydroxy phenyl butanone crystals; 2.00–4.00% 3-(1-methyl-ethyl) bicyclo (2,2,1) hept-5-ene-2-carboxylic acid ethyl ester; 2.00–4.00% 4-methyl-2-phenyl-3,6-dihydropyrane based on the total weight of a fragrance component of the cosmetic composition, wherein the total amount of fragrance enhancing composition added is in the range of 5.2–10.7% based on the total weight of the fragrance component.

2. A cosmetic composition made with a fragrance enhancing composition comprising 0.05–0.30% 4-hydroxy-3-methoxy benzaldehyde; 0.05–0.30% pyrimidine, 2,4-diethoxy-5-methyl; 0.05–0.30% 3aR-(3aalpha,5a,alpha,9a, beta,9b,beta))-dodecahydro-3a,6,6,9a-tetramethyl-naphthto (2,1-b)furan; 0.05–0.30% benzenepropanal, 4-ethyl-alpha, alpha-dimethyl; 0.05–0.30% Vetiver Oil Java; 2.00–4.00% Iso Methyl Cedryl Ketone A; 2.00–4.00% 1-methyl-4-isopropyl-1-cyclohexen-8-ol; 3.006.00 Patchouli Oil; and 6.00–10.00% amyl cinnamic aldehyde, based on the total weight of a fragrance component of the cosmetic composition, wherein the total amount of fragrance enhancing composition added is in the range of 13.2–25.5% based on the total weight of the fragrance component.

3. A cosmetic composition made with a fragrance enhancing composition comprising 0.05–0.30% 2-buten-1-one, 1-(2,6,6-trimethyl-2-cyclohexen-1-yl); 0.05–0.30% cyclohexanol, 2-(1,1-dimethylethyl)-4-methyl-; 0.05–0.30% L-1-methyl-4-isopropenyl-6-cyclohexene-2-one; 0.40–0.90% benzyl propionate; 1.00–2.00% 2-methyl-3-(para-isopropylphenyl) propionaldehyde; 3.00–6.00% Orange Oil Morocco; 3.00–6.00% 3–7-dimethyl-6-octen-1-ol; 3.00–6.00% Pelargonyl, based on the total weight of a fragrance component of the cosmetic composition, wherein the total amount of fragrance enhancing composition added is in the range of 10.6–21.8% based on the total weight of the fragrance component.

4. A cosmetic composition made with a fragrance enhancing composition comprising 0.005–0.05% nonyl aldehyde; 0.005–0.05% decyl aldehyde; 0.05–0.30% cis-3-hexenyl salicylate; 0.05–0.30% 3,7-dimethyl-2,6-octadienal; 0.40–0.90% 2-methyl-3-(para-isopropylphenyl) propionaldehyde; 1.00–2.00% 3–7-dimethyl-6-octen-1-ol; 1.00–2.00% methyl ionone (mixture of isomers), based on the total weight of a fragrance component of the cosmetic composition, wherein the total amount of fragrance enhancing composition added is in the range of 2.5–5.6% based on the total weight of the fragrance component.

5. A cosmetic composition made with a fragrance enhancing composition comprising 0.05–0.30% isobutyl quinoleine; 0.05–0.30% 3aR-(3a,alpha,5a,alpha,9a,beta,9b,beta))-dodecahydro-3a,6,6,9a-tetramethyl-naphthto(2,1-b) furan; 0.6–1.00% Cinnamon Leaf Oil Ceylan; 0.6–1.00% 2-methoxy-4-allyl phenol; 2.00–4.00% Iso Methyl Cedryl Ketone A; and 3.00–6.00% Patchouli Oil, based on the total weight of a fragrance component of the cosmetic composition, wherein the total amount of fragrance enhancing composition added is in the range of 6.3–12.6% based on the total weight of the fragrance component.

6. A cosmetic composition made with a fragrance enhancing composition comprising 0.05–0.30% 4-isopropyl-1-methyl cyclohexan-3-one; 0.05–0.30% 3-ethoxy-4-hydrobenzaldehyde; 0.15–0.40% decyl aldehyde natural; 1.00–2.0% 5-methyl-2-isopropyl cyclohexanol; 1.00–2.00% 3-buten-2-one, 3 methyl-4-(2,6,6-trimethyl-2-cyclohex-1-yl; 3.00–6.00% 2-trans-3,7-dimethyl-2,6-octadien-8-ol, based on a total weight of fragrance component of the cosmetic composition, wherein the total amount of fragrance enhancing composition added is in the range of 5.30–11.00% based on the total weight of the fragrance component.

* * * * *